(12) United States Patent
Putz

(10) Patent No.: US 7,277,742 B2
(45) Date of Patent: Oct. 2, 2007

(54) CORTICAL ELECTRODE SUPPORT ASSEMBLY

(75) Inventor: David A. Putz, Pewaukee, WI (US)

(73) Assignee: Ad-Tech Medical Instrument Corporation, Racine, WI (US)

( * ) Notice: Subject to any disclaimer, the term of this patent is extended or adjusted under 35 U.S.C. 154(b) by 302 days.

(21) Appl. No.: 11/132,487

(22) Filed: May 19, 2005

(65) Prior Publication Data

US 2006/0264728 A1  Nov. 23, 2006

(51) Int. Cl.
*A61B 5/04*  (2006.01)

(52) U.S. Cl. .................. 600/378; 600/383; 607/116; 607/139

(58) Field of Classification Search ............... 600/378, 600/383; 607/116, 139
See application file for complete search history.

(56) References Cited

U.S. PATENT DOCUMENTS 2,549,836 A * 4/1951 McIntyre et al. ........... 600/383
6,167,145 A * 12/2000 Foley et al. ................ 600/383

* cited by examiner

*Primary Examiner*—Lee S. Cohen
(74) *Attorney, Agent, or Firm*—Jansson Shupe & Munger Ltd.

(57) ABSTRACT

A cortical electrode support assembly is provided having at least one cortical sensing device, preferably an electrode device, a connector and a support apparatus. The cortical sensing device includes at least one sensing element, preferably a contact, and a lead with a connection member that is preferably a socket extending from the contact. The connector has a connecting element that is preferably a connecting pin adapted to receive the connection member and a electrical conduit extending from it. The support apparatus is provided with an adjustable clamp and a mount that has the connector secured to it. The electrical conduit preferably has an input jack for connecting it to an external device such as an external monitoring device. Preferably, the support apparatus also includes a post on which the mount is slidably secured at one end and the clamp is adjustably attached to the other end. A method of monitoring brain activity during brain surgery is also disclosed.

22 Claims, 3 Drawing Sheets

CORTICAL ELECTRODE SUPPORT ASSEMBLY

FIELD OF THE INVENTION

This invention is related generally to brain surgery support devices and, more particularly, to cortical electrode support assemblies.

BACKGROUND OF THE INVENTION

A variety of cortical electrode devices, including strip electrodes, are available to be placed upon the surface of the brain for a number of neurological purposes including monitoring brain activity during open brain surgery. Leads extend outward from these electrodes to enable the electrodes to be joined to external devices such as monitoring equipment. This link is usually accomplished through the use of connectors since they are designed to accommodate a plurality of leads needed to electrically communicate with a range of medical equipment located at a distance from the electrodes.

Certain connectors in the prior art have, however, various shortcomings and problems. Some of these devices require multiple parts to achieve connection of each lead to the connector. This adds to the complexity of their operation and makes difficult any attempts at one-handed connection or disconnection. Simplicity in structure and operation is particularly important when considering that repeated connections and disconnections may need to occur during surgery at a time when the surgeon and his staff are already giving attention to a great many other matters. This added complexity in the operational procedures needed to be carried out by one or more medical personnel is therefore a significant shortcoming to use of these connectors.

Maintaining a reliable and constant connection to each electrode device throughout the period of their use is another important consideration. Connectors not providing a definitive visual indication that electrical connection has been accomplished can be problematic. Another concern is that inadvertent disconnection or dislodging of the contact between the connector with the leads from the electrode devices or the unexpected destruction of the connection between the leads and the devices themselves can too often occur. This is a serious problem because, with certain connectors, such events may make it difficult or even impossible for the physician or technician to quickly re-establish a connection between the electrode with the external medical equipment when reliance upon that device, as during surgery, is critical.

Contributing to these difficulties is the absence in most cases of convenient access to the connector being used since these devices are usually located at a distance from the immediate surgical site. A connector that can be mounted in close proximity to the cortical electrodes for immediate accessibility to the surgical staff would then be highly desirable.

This invention addresses many of these problems and shortcomings in a simple and inexpensive manner.

OBJECTS OF THE INVENTION

It is a primary object of this invention to provide a cortical electrode support assembly that overcomes some of the problems and shortcomings of the prior art.

Another object of this invention is to provide a novel cortical electrode support assembly that provides easy access during brain surgery to the connector and its connections to each of the attached cortical electrode devices.

Another object of this invention is to provide an exceptional cortical electrode support assembly that allows for quick and easy connection of cortical electrode devices to medical monitoring equipment during surgery as well as for the re-connection of these electrode devices when inadvertently disconnected.

Another object of this invention is to provide an excellent cortical electrode support assembly that can be quickly and with minimal effort firmly clamped to the skull and then later loosened for relocation to another spot upon the skull using just one hand.

Another object of this invention is to provide a desirable cortical electrode support assembly that allows the orientation of the leads from the cortical electrode devices as they exit the surgical site to be easily redirected.

Yet another object of this invention is to provide an improved cortical electrode support assembly that is simple to construct, easy to maintain, and highly reliable to use.

SUMMARY OF THE INVENTION

This invention is for a cortical electrode support assembly having at least one cortical sensing device, a connector and a support apparatus. The cortical sensing device includes at least one sensing element and a lead with a connection member extending from the sensing element. The connector has a connecting element adapted to receive the connection member and a electrical conduit extending from this element. The support apparatus is provided with an adjustable clamp sized to clamp to the skull during open brain surgery and a mount having the connector secured to it.

Most desirable is where the sensing device is an electrode device, the sensing element is a contact, the electrode device has only one contact, and where the connection member is a socket that attaches to a connecting pin for the connecting element. Sensing elements may also include chemical sensors and optical sensors to monitor chemical activity, temperature and blood flow within the cortex. These sensors can be used in place of or in combination with an electrical contact on various sensing devices.

More desirable is where the electrical conduit has an input jack to connect it with an external device. In certain highly desirable embodiments, the contact senses or stimulates cortical electrical activity and the external device is an external monitoring device adapted to monitor brain activity.

In a preferred embodiment, the support apparatus also includes a post where the mount is slidably secured at the distal end and the clamp is adjustably attached to the proximal end. Most preferred embodiments find the clamp having upper and lower clamping portions. The lower clamping portion extends from the proximal end and the upper clamping portion is slidably mounted to the post in a manner where it is in registry with the lower clamping portion. The upper clamping portion is free to extend and retract axially along the post between limits. In some highly preferred embodiments, the lower clamping portion includes a substantially smooth lower clamping surface and the upper clamping portion has a substantially serrated upper clamping surface.

More preferred in these embodiments is where the support apparatus includes an adjustment member threadably disposed to a threaded portion of the post at a position between the mount and the upper clamping portion. The limit of extension for the upper clamping portion is established by the presence of the adjustment member along the post. The adjustment member often has a threaded bore that is coaxial with the post and sized to receive its threaded portion.

In another embodiment that is desired, the assembly finds the sensing device being a plurality of electrode devices, the sensing element being a contact, and each of these electrode devices having only one contact. In this embodiment, the connection member on each lead is a socket and the connecting element comprises a plurality of connecting pins. Each pin is sized to receive any of these sockets and has one of a plurality of electrical conduits extending from it. More desirable is where each of the electrode devices has indicia to distinguish one device from the other. Very preferred is where each conduit has an input jack connecting the conduit to an external device and each pin and the corresponding input jack have the same indicia. This distinguishes one pin from the other and identifies the electrical conduit associated with each pin. Highly preferred is where the indicia are numerical.

Another aspect of the invention is directed to a method for monitoring brain activity during brain surgery. This method includes the steps of (1) providing at least one cortical electrode device supporting a contact and having a lead with a connecting member extending from the contact; (2) guiding the electrode device through an opening made in the skull so as to place it upon the surface of the brain during open brain surgery at a desired position for sensing brain activity; (3) clamping a support apparatus to the skull where the support apparatus has a connector attached to it and where the connector includes at least one connecting element, each element being sized to receive the connecting member and having an electrical conduit with an input jack extending from it; (4) attaching the connecting member to the connecting element; (5) inserting the input jack into an external monitoring device; (6) sensing brain activity with the contact; and (7) recording the sensed brain activity during the surgery with the external monitoring device.

Preferred is where the support apparatus includes a mount to which the connector is rigidly secured and a clamp sized to receive the skull. The mount is slidably secured to the distal end of a post and the clamp is adjustably attached to the proximal end of this post. More preferred are embodiments finding the clamp having upper and lower clamping portions and the clamping step has the skull being placed between the upper and lower portions. The lower clamping portion extends from the proximal end and the upper clamping portion is slidably mounted to the post in a manner where it is in registry with the lower clamping portion and free to slide up and down along the post.

Most preferred in these embodiments is where the support apparatus also includes an adjustment member threadably disposed upon a threaded portion of the post between the mount and the upper clamping portion. Screwing the adjustment member downward toward the clamp forces the upper clamping portion into the skull.

Certain embodiments find a plurality of electrode devices with a single contact being provided where the connecting member on each device is a socket and the connecting element on the connector is a plurality of connecting pins. In these embodiments, each pin is adapted to receive the socket from at least one of the devices and one of a plurality of electrical conduits extends from each pin. More preferred is where each pin is adapted to receive the socket from any electrode device.

Most desirable is where the pins and the corresponding input jacks have identical indicia. In this manner, the indicia on each input jack identifies the pin electrically connected to the external monitoring device to which the input jack is inserted. These embodiments further add the step of choosing the external monitoring device such that the attaching step includes the selection of the pin corresponding to the chosen monitoring device. Highly desirable is where the electrode devices also have indicia and the attaching step includes matching the indicia on one of the devices with the indicia on one of the pins.

In certain preferred embodiments, the method adds the step of replacing the electrode device with another cortical electrode device and has the choosing step include choosing the monitoring device electrically connected to the device being replaced. Highly preferred in these embodiments is where the electrode device being replaced has a broken lead.

DETAILED DESCRIPTION OF PREFERRED EMBODIMENTS

Figure 1:
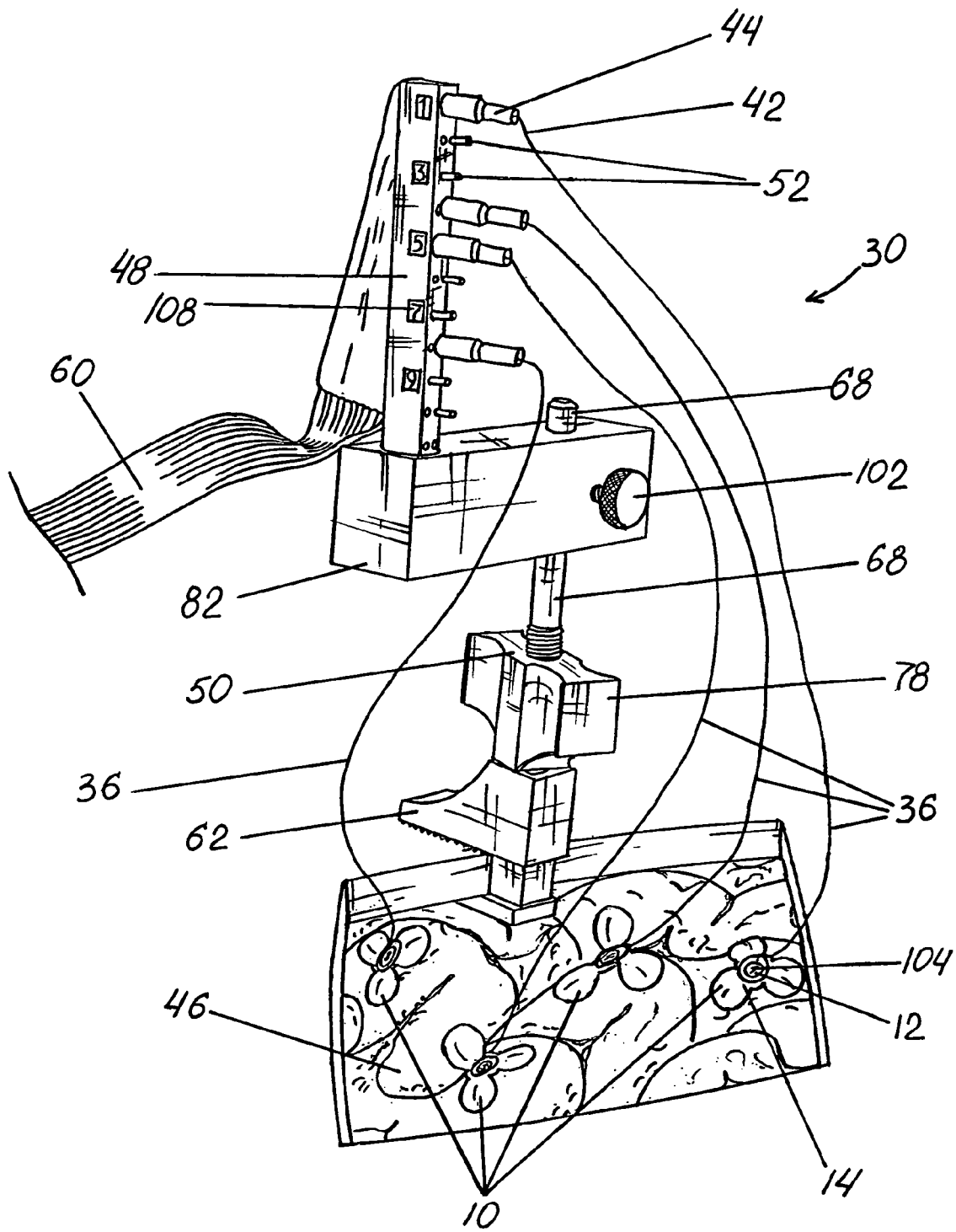
FIG. 1 is a perspective view of the cortical electrode support assembly in accordance with this invention.

FIG. 1 is a perspective view of a cortical electrode support assembly 30 having a preferred embodiment in accordance with this invention. Cortical electrode support assembly 30 includes cortical electrode device 10, connector 48 and support apparatus 50. Cortical electrode device 10 as shown includes contact 12 secured to support member 14. Contact 12 is preferably platinum or stainless steel and can be utilized to measure brain electrical activity within the cortex or provide electrical stimulation to a select tissue region.

Figure 2:
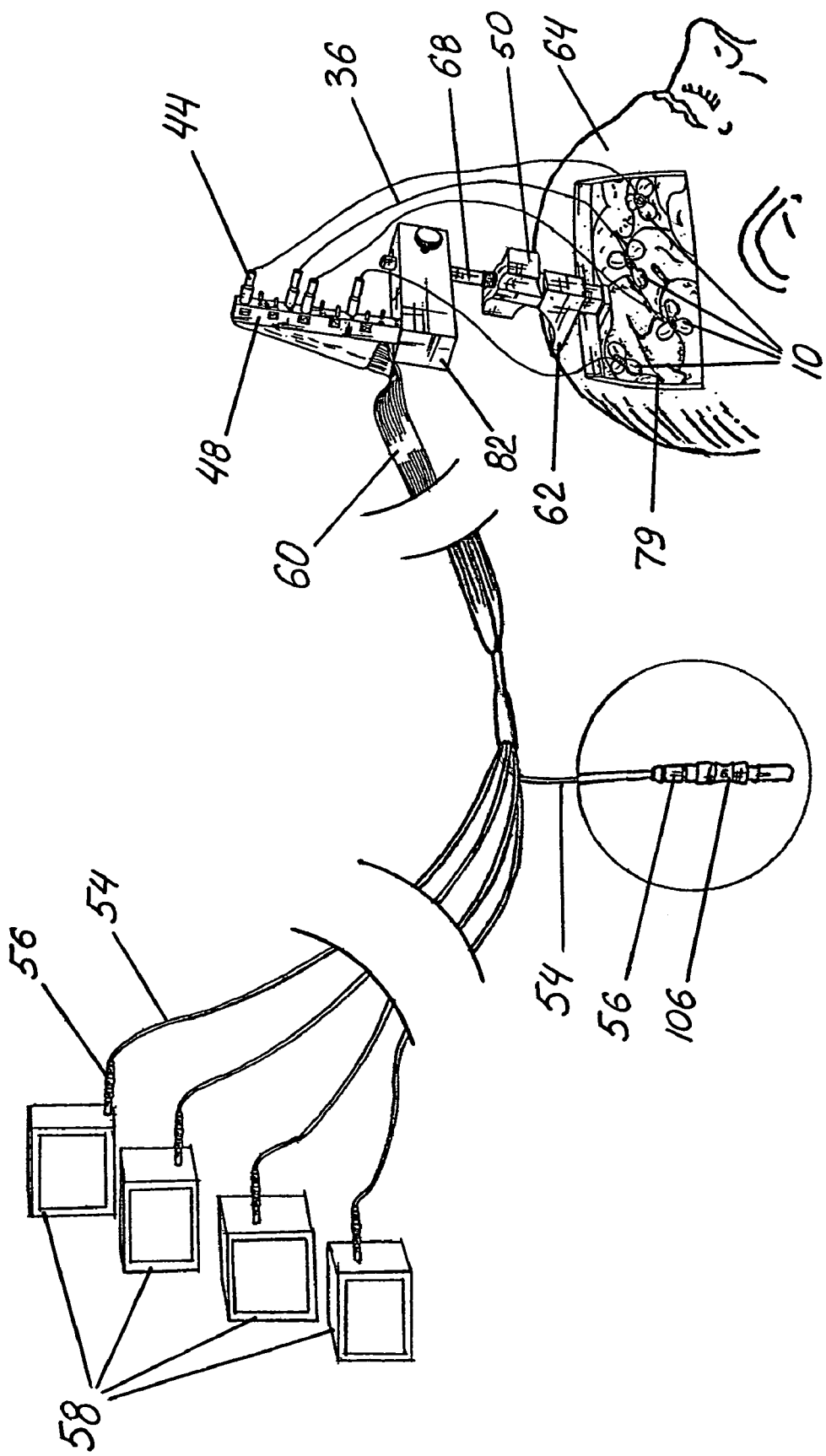
FIG. 2 is a schematic view illustrating the connection of the cortical electrode devices of FIG. 1 to external devices through the connector and electrical conduit in accordance with this invention and with an enlarged view of an input jack on the electrical conduit.

Support member 14 is provided with a circular opening sized to receive contact 12 in a manner where a lower surface (not shown) protrudes downward from and is not covered by support member 14. As seen in FIGS. 1 and 2, this configuration enables contact 12 to directly touch the surface 46 of the brain when placed through an opening 79 in the skull onto the cerebral cortex.

Support member 14 is preferably formed from a dielectric material that is both flexible and bio-compatible. A silicone material such as a medical grade of SILASTIC® is desirable although an equivalent dielectric elastomer can also be used. The material is also preferably transparent to enable the underlying features of the cortical surface to be visualized when electrode device 10 is placed upon the brain.

A proximal end of a single lead 36 is electrically secured to contact. Distal end 42 of lead 36 is electronically attached to socket 44.

Figure 3:
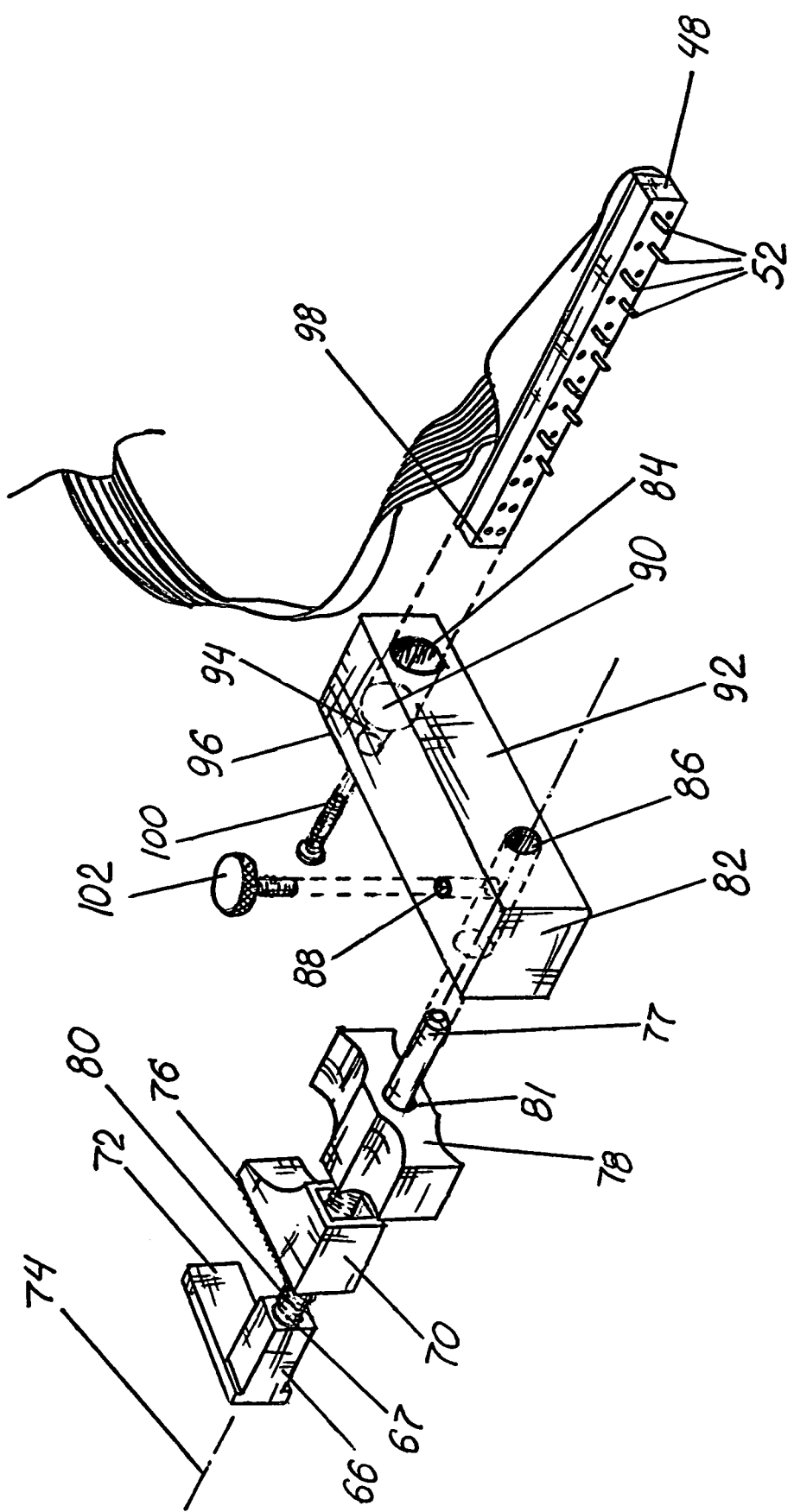
FIG. 3 is an exploded view of the support apparatus in FIG. 1 with the connector disengaged from the mount.

FIGS. 1 and 2 illustrate a number of electrode devices 10 positioned upon the surface 46 of the cerebral cortex following a craniotomy. Sockets 44 of each lead 36 have a tapered interior to snugly receive a connector pin 52 on connector 48 in frictional engagement. As seen in FIGS. 1-3, connector 48 is provided with a plurality of connecting pins 52. Each pin 52 is in electrical communication with an electrical conduit 54, each wire conduit 54 having an input jack 56 attached at the end opposite from the corresponding connecting pin 52.

Input jack 56 enables the electrical conduit 54 and thereby the associated electrode device 10 to be connected to an external device 58. Where electrode device 10 is intended to monitor electrical brain activity, external device 58 will preferably consist of a conventional monitoring device with output display and a suitable power source to record or display information communicated by electrode device 10. Electrical conduits 54 preferably combine to form a conduit ribbon 60 upon exiting connector 48 so that individual loose wires can be avoided. As seen in FIG. 2, conduit ribbon 60 separates into the individual electrical conduits 54 at a distance from connector 48 to enable one or more input jacks 56 to be electronically attached to the necessary external devices 58.

Connector 48 is mounted to support apparatus 50 to provide better access to connector 48 during treatment of a patient. As illustrated in FIGS. 1 and 2, support apparatus 50 includes a clamp 62 capable of attaching support apparatus 50 to the skull 64. Clamp 62 comprises a lower clamping portion 66 forming the proximal end 67 of a post 68 and an upper clamping portion 70 slidably disposed upon post 68. FIG. 3 shows that lower clamping portion 66 has a smooth lower clamping surface 72 extending outward from axis 74 of post 68. Upper clamping portion 70 is provide with a serrated upper clamping surface 76 that is in registry with lower clamping surface 72. Clamp 62 can also easily attach support apparatus 50 to many of the cranial stabilization and retractor assemblies utilized when performing invasive head surgery.

In mounting support apparatus 50 to the skull 64, the spacing between both clamping surfaces 72,76 is increased by sliding upper clamping portion 70 in the direction of the distal end 77 of post 68. Lower clamping portion 66 is inserted into an opening 79 in skull 64 so that lower clamping surface 72 can be placed up against the interior surface of skull 64. Upper clamping portion 70 is then lowered to bring upper clamping surface 76 in contact with the exterior surface of skull 64.

Support apparatus 50 includes adjustment member 78 to stop upper clamping portion 70 from sliding upward and to maintain upper and lower clamping portions 66,70 firmly in contact with skull 64. Adjustment member 78 has a threaded bore 81 that is threadably mounted upon post 68 along a threaded portion 80 adjacent to lower clamping portion 66. Adjustment member 78 can then be rotated in a conventional manner so that adjustment member 78 is forcefully urged against upper clamping portion 70 to reduce the spacing between clamping portions 66,70 and thereby firmly tighten clamp 62 upon skull 64.

Support apparatus 50 also includes mount 82. As seen in FIG. 3, mount 82 is provided with three apertures 84,86,88. First aperture 84 is at one end of mount 82 and has a top portion 90 opening onto top surface 92 and a bottom portion 94 opening onto bottom surface 96. Portions 90,94 are coaxial but have different diameters. Top portion 90 is sized to receive the bottom end 98 of connector 48 so that connector 48 can then be secured to mount 82 by having a fastener 100, preferably a screw, threadably engage bottom end 98 through bottom portion 94.

Second aperture 86 is at the other end of mount 82 and extends from top surface 92 to bottom surface 96. Second aperture is adapted to receive the distal end 77 of post 68. Third aperture 88 is orthogonal to and in communication with second aperture 86. Third aperture 88 is sized to threadably receive a grip screw 102. Post 68 is firmly secured within mount 82 by threadably advancing grip screw 102 within third aperture 88 until grip screw 102 is urged into contact with and frictionally engages post 68. One can readily see that mount 82 can be raised or lowered along post 68 or pivoted about post 68 before grip screw 102 is tightened so that a desirable position for mount 82 in relation to skull 64 and thereby the adjacent surgical field can be achieved.

As shown in FIG. 2, each input jack 56 is numbered, preferably with a collar 106 embedded with numerical indicia. Likewise, a numerical decal 108 is fastened on the connector 48 adjacent to each connecting pin 52. The number on the collar 106 of each input jack 56 is the same number found on the decal 108 corresponding to the connecting pin 52 that is connected via electrical conduit 54 to that specific input jack 56. One can appreciate that in this manner the physician or technician can immediately identify which electrode device 10 is being monitored by a specific external device 58 by matching the number on the collar 106 of the input jack 56 connected to that device with the corresponding number on the connector 48 to see which electrode device 10 is engaged to the connecting pin 52 associated with that number. In a similar fashion, the connecting pin 52 associated with a certain desired external device 58 can be easily identified when attaching electrode devices 10 to connector 48 or when replacing one electrode device 10 with another such as when a lead breaks or contact 12 becomes inoperative.

Electrode devices 10 are also provided with numerical indicia 104 to use to distinguish one electrode device from the others. Although the physician or technician remains free to attach the socket 44 for a given electrode device 10 to any empty or unattached connecting pin 52 on the connector 48, connecting the socket 44 to the connecting pin 52 having a number on the adjacent decal 108 that matches the number on the electrode device 10 itself will permit that individual to more quickly, easily and with greater assurance associate each electrode device 10 with a corresponding external device 58.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A cortical electrode support assembly comprising:
   at least one cortical sensing device having at least one sensing element and a lead extending from the sensing element, the lead having a connection member;
   a connector having at least one connecting element adapted to receive the connection member and at least one electrical conduit extending from the connection element; and
   a support apparatus having an adjustable clamp sized to receive a skull and a mount having the connector secured with respect thereto, whereby the apparatus can be clamped to the skull during open brain surgery.

2. The assembly of claim 1 wherein the sensing device is an electrode device, the sensing element is a contact, the electrode device has only one contact, the connection member on the electrode device is a socket and the connecting element is a connecting pin.

3. The assembly of claim 2 wherein the electrical conduit has an input jack that electrically connects the electrical conduit with respect to an external device.

4. The assembly of claim 3 wherein the contact is adapted to sensing or stimulating cortical electrical activity and the external device is an external monitoring device adapted to monitor brain activity.

5. The assembly of claim 1 wherein the support apparatus further includes a post having an axis and proximal and distal ends, the mount being slidably secured with respect to the distal end and the clamp being adjustably secured to the proximal end.

6. The assembly of claim 5 wherein the clamp includes upper and lower clamping portions, the lower clamping portion extending from the proximal end and the upper clamping portion being slidably mounted with respect to the post in registry with the lower clamping portion, the upper clamping portion being free to extend and retract axially along the post between limits.

7. The assembly of claim 6 wherein the support apparatus further includes an adjustment member threadably disposed with respect to a threaded portion of the post and defining a position between the mount and the upper clamping portion, whereby the limit of extension for the upper clamping portion is set by the position of the adjustment member along the post.

8. The assembly of claim 7 wherein the lower clamping portion has a substantially smooth lower clamping surface and the upper clamping portion has a substantially serrated upper clamping surface.

9. The assembly of claim 1 wherein the sensing device is a plurality of electrode devices, the sensing element is a contact and each electrode device has only one contact, the connection member on each electrode device is a socket, the connecting element is a plurality of connecting pins, each pin adapted to receive the socket from any of the electrode devices, and the electrical conduit is a plurality of electrical conduits, each conduit extending from one of the pins.

10. The assembly of claim 9 wherein each electrode device includes indicia distinguishing one electrode device from the other.

11. The assembly of claim 10 wherein each conduit has an input jack connecting the conduit to an external device and each pin and the corresponding input jack have identical indicia to distinguish one pin from the other.

12. The assembly of claim 11 wherein the indicia are numbers.

13. A method of monitoring brain activity during brain surgery comprising:
  providing at least one cortical electrode device supporting at least one contact and having a lead with a connecting member extending from the contact;
  guiding the electrode device through an opening in a skull to a position upon a surface of a brain such that the contact is at a desired location for sensing brain activity;
  clamping a support apparatus to the skull, the support apparatus having a connector secured thereto, the connector having at least one connecting element sized to receive the connecting member, the connecting element having at least one electrical conduit with an input jack extending therefrom;
  attaching the connecting member to the connecting element;
  inserting the input jack into an external monitoring device;
  sensing brain activity with the contact;
  recording the sensed brain activity during the surgery with the external monitoring device.

14. The method of claim 13 wherein the support apparatus includes a mount that has the connector rigidly secured thereto, a clamp adapted to receive the skull, and a post having an axis and proximal and distal ends, the mount being slidably secured with respect to the distal end and the clamp being adjustably secured to the proximal end.

15. The method of claim 14 wherein the clamp includes upper and lower clamping portions, the lower clamping portion extending from the proximal end and the upper clamping portion being slidably mounted with respect to the post in registry with the lower clamping portion, the upper clamping portion being free to extend and retract axially along the post and the clamping step further includes placing the skull between the upper and lower clamping portions.

16. The method of claim 15 wherein the support apparatus further includes an adjustment member threadably disposed to a threaded portion of the post between the mount and the upper clamping portion such that rotation of the adjustment member urges the upper clamping portion into the skull.

17. The method of claim 13 wherein the providing step includes a plurality of electrode devices, each electrode device having only one contact, the connection member on each electrode device is a socket, the connecting element is a plurality of connecting pins, each pin adapted to receive the socket from at least one of the electrode devices, and the electrical conduit is a plurality of electrical conduits, each conduit extending from one of the pins.

18. The method of claim 17 wherein each pin is adapted to receive the socket from any of the electrode devices.

19. The method of claim 18 wherein the pins and the corresponding input jacks have identical indicia such that the indicia on each input jack identifies the pin electrically connected to the external monitoring device to which the input jack is inserted and further comprising choosing the external monitoring device wherein the attaching step further includes selecting the pin corresponding to the chosen monitoring device.

20. The method of claim 19 further comprising replacing the electrode device with another cortical electrode device wherein the choosing step further includes choosing the monitoring device electrically connected to the electrode device being replaced.

21. The method of claim 20 wherein the electrode device being replaced has a broken lead.

22. The method of claim 19 wherein the electrode devices have indicia and the attaching step further includes matching the indicia on at least one of the electrode devices with the indicia on at least one of the pins.

* * * * *